United States Patent
Wunderling et al.

[11] Patent Number: 6,072,577
[45] Date of Patent: Jun. 6, 2000

[54] NOBLE GAS DETECTION AND DETERMINATION

[75] Inventors: Martin Wunderling, Herrenberg; Bernhard Fischer, Leonberg; Siegfried Kaestle, Nufringen, all of Germany

[73] Assignee: Hewlett-Packard Company, Palo Alto, Calif.

[21] Appl. No.: 09/282,985

[22] Filed: Mar. 31, 1999

[30] Foreign Application Priority Data

Apr. 21, 1998 [EP] European Pat. Off. ............. 98107198

[51] Int. Cl.[7] .................................................... G01J 3/44
[52] U.S. Cl. ............................................................. 356/301
[58] Field of Search ................................... 356/301, 303, 356/320, 326

[56] References Cited

U.S. PATENT DOCUMENTS

| | | | |
|---|---|---|---|
| 4,664,522 | 5/1987 | LeFebre | 356/328 |
| 4,784,486 | 11/1988 | Van Wagenen et al. | 356/301 |
| 5,179,420 | 1/1993 | So et al. | 356/73.1 |
| 5,341,206 | 8/1994 | Pittaro et al. | 356/301 |
| 5,515,169 | 5/1996 | Cargill et al. | 356/417 |
| 5,644,417 | 7/1997 | Aulet et al. | 359/110 |
| 5,788,893 | 7/1998 | Fink et al. | 356/301 |

FOREIGN PATENT DOCUMENTS

| | | |
|---|---|---|
| 0453176A2 | 4/1991 | European Pat. Off. . |
| 0548935A1 | 12/1992 | European Pat. Off. . |
| 0 600 711 A2 | 11/1993 | European Pat. Off. . |
| 0 658 759 A1 | 12/1994 | European Pat. Off. . |
| 06140717 | 5/1994 | Japan . |

OTHER PUBLICATIONS

European Search Report, EP 98 10 7197, Nov. 3, 1998.

*Primary Examiner*—Frank G. Font
*Assistant Examiner*—Layla Lauchman

[57] ABSTRACT

Disclosed is the determining of a composition of a gas mixture comprising an amount of one or more noble gases. A Raman spectrum of the gas mixture is measured first, and the amount(s) of Raman-active gas(es) in the gas mixture are determined based on the measured Raman spectrum. The amount of the (Raman non-active) one or more noble gases in the gas mixture can then be determined from the determined amount(s) of Raman-active gas(es). The composition of the gas mixture can also be determined by analyzing the Raman scattering in combination with the Rayleigh scattering. Based on the measured Raman spectrum, the expected intensifies of the Rayleigh lines of the Raman-active gases in the gas mixture are determined. The amount of the noble gas in the gas mixture is represented by the difference of the summed up Rayleigh lines of the Raman-active gases to the Rayleigh line in the measured spectrum.

16 Claims, 1 Drawing Sheet

NOBLE GAS DETECTION AND DETERMINATION

BACKGROUND OF THE INVENTION

The present invention relates to the determining of a composition of a gas mixture comprising an amount of one or more noble gases.

Gas detection, in general, is accomplished either by using optical absorption or by scattering of light For absorption measurements, primarily the infrared (IR) spectral region is used, where the excitation of molecular vibrations contributes to the dipole moment of a molecule. Atomic gases, such as the noble gases, do not exhibit IR absorption. Scattering of light occurs as a consequence of the electronic polarizability of the electron cloud around atoms and molecules. The law of photometric summation applies, so that the total energy scattered by N molecules is just N times the energy scattered by one molecule.

Most incident photons are scattered by the sample with no change in frequency in a process known as Rayleigh scattering. Rayleigh scattering occurs from molecular as well as atomic species. However, with a small probability the scattered photons have frequencies $f_0+/-f_1$, where $f_0$ is the frequency of the incident photon and $f_1$ is the frequency of a molecular vibration. This process is called Raman scattering. The modification of the scattered photons results from the incident photons either gaining energy from or losing energy to the vibrational or rotational motion of the molecule. Since complex molecules exist in a number of different rotational and vibrational states (depending on the temperature), many different values of $f_1$ are possible. Consequently, the Raman spectrum of a Raman-active gas will consist of a large number of scattered lines. Simple diatomic molecules like oxygen, $O_2$, or nitrogen, $N_2$, have just one Raman line.

To enhance the observation of the radiation at $f_0+/-f_1$, the scattered radiation is observed perpendicularly to the incident beam. To provide high intensity incident radiation and to enable the observation of lines where $f_1$ is small (due to rotational changes), the source of a Raman spectrometer is normally chosen as a monochromatic visible laser. The scattered radiation can then be analyzed by use of a scanning optical monochromator with a photomultiplier tube or another suitable photo detector.

Noble gases have stable electron configurations and thus do not easily gain or lose electrons and rarely share them with other elements. Therefore, noble gases exist only as mono-atomic species that do not have any vibrational states and consequently do not give rise to Raman scattering, so that noble gases are generally Raman non-active.

A possibility for noble gas detection as known in the art is the resonanceionization mass spectrometry (RIS). However, RIS can be applied to the inert or noble gases only with great difficulty due to the short wavelength required for the first excitation step.

Xenon (Xe), as a noble gas, has been investigated as an anaesthetic gas and has been proved as a possible anesthesia means substantially free of side effects and innocuous for the earth atmosphere and environment. Clinical tests for medical applications are underway e.g. in Germany.

A general difficulty with applying xenon as a component of a respiration gas is the required measuring technique for a quantitative monitoring of the xenon concentration. Respiration gas monitors as known in the art are generally based on infrared absorption and allow detecting $CO_2$, $N_2O$, and other commonly applied volatile anesthetics (e.g. halothane, enflurane, isoflurane, desflurane, and sevoflurane). Oxygen ($O_2$) is detected with separate measuring cells, e.g. making use of the paramagnetic properties of oxygen. Nitrogen ($N_2$) cannot be detected with those monitors. As pointed out above, noble gases, such as xenon, are not detectable by measuring methods applying infrared and can only be detected by mass spectrometry, which, however, requires expensive monitors, and are thus normally not applicable for standard applications in hospitals.

SUMMARY OF THE INVENTION

It is an object of the present invention to provide a low cost possibility for determining a noble gas concentration. This object is solved by the independent claims. Preferred embodiments are set out in the dependent claims.

According to the invention, a composition of a gas mixture comprising an amount of one or more noble gases is determined by first measuring a Raman spectrum of the gas mixture. The contribution of the Raman-active gas(es) to the Raman spectrum of the gas mixture, with respect to reference spectra of the Raman-active gas(es), allows to draw back conclusions on the amount of Raman-active gas(es) in the gas mixture, and thus, on the amount of the one or more (Raman non-active) noble gases in the gas mixture.

According to a first aspect of the invention, the measured Raman spectrum is compared with one or more reference spectra. The proportion of the measured spectrum to the reference spectrum or to each one of the reference spectra provides a measure for the proportion of the gas component represented by the respective reference spectrum in the gas mixture. The proportion of the gas component can be determined by comparing one or more peaks of the measured Raman spectrum with one or more peaks in the one or more reference spectra, preferably by comparing the amplitudes and/or intensities of the peaks. The amounts of the Raman-active gases in the gas mixture can thus be summed up and subtracted from the total amount of the gas mixture, whereby the subtracted amount represents the amount of the one or more noble gases.

According to a second aspect of the invention, the composition of the gas mixture is determined by analyzing the Raman scattering in combination with the Rayleigh scattering. Based on the measured Raman spectrum, the expected intensities of the Rayleigh lines of the Raman-active gases in the gas mixture are determined. The amount of the noble gas in the gas mixture is represented by the difference of the summed up Rayleigh lines of the Ramanactive gases to the Rayleigh line in the measured spectrum.

According to a third aspect of the invention, the result of the determining according to the first aspect can be checked using the determining according to the second aspect with the Rayleigh lines of the measured spectrum and the reference spectrum. In case that the intensity of the summed up individual Rayleigh lines equals the intensity of the measured Rayleigh line, the composition of a gas mixture has been determined correctly.

The aspects of the invention can be used as well for a quantitative noble gas determination as for a qualitative noble gas detection e.g. in case that a quantitative evaluation is not required.

The invention is preferably used in a respiration gas monitor for medical purposes preferably for monitoring noble gas constituents such as xenon.

BRIEF DESCRIPTION OF THE DRAWINGS

Other objects and many of the attendant advantages of the present invention will be readily appreciated and become better understood by reference to the following detailed description when considering in connection with the accompanied drawing in which.

DETAILED DESCRIPTION OF THE INVENTION

According to the first aspect of the invention, a composition of a gas mixture comprising an unknown amount of a known noble gas (which is not "Ramanactive") and an unknown amount of a number of other gas constituents (which are "Raman-active") is determined by quantitatively determining the amounts of all Raman-active gases and thus recalculating the amount of the Raman non-active noble gas.

Figure 1:
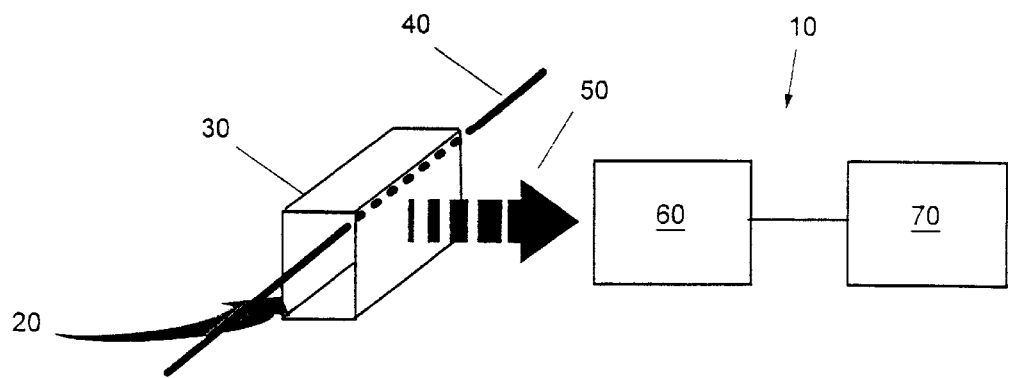
FIG. 1 depicts the schematic of a gas monitor according to the invention.

FIG. 1 depicts the schematic of a gas monitor 10 according to the invention. A gas flow 20 is directed through a sample cell 30 An incident light beam 40, e.g. from a laser source, is scattered in the sample cell 30 and a scattering light 50 is received by a spectrograph 60. The spectrograph 60 is further coupled to a processing unit 70 for determining the composition of the gas mixture in the gas flow 20.

The processing unit 70 is preferably further connected (not shown) to the source of the light beam 40 for receiving information about the light beam 40, s such as the intensity. The processing unit 70 is preferably further coupled to a (not shown) pressure determining means and a temperature sensor within the sample cell 30 for receiving information about the pressure and temperature therein.

In a first step, the spectrograph 60 of the gas monitor 10 measures the Raman spectrum of the gas mixture and the measured spectrum is then compared with one or more reference spectra of the individual gas components. Each reference spectrum represents the Raman spectrum for the pure gas component, determined under known conditions, e.g. a known condition of pressure and/or temperature within the sample cell 30 and of the intensity of 1s the incident light beam 40. Accordingly, reference spectra can be applied already representing a defined gas mixture. The proportion of the measured spectrum to each reference spectrum provides a direct measure of the proportion of the individual gas component (represented by the reference spectrum) in the gas mixture.

In case that more than one Raman-active component has been detected in the measured spectrum, the proportions of the individual gas components are summed up and subtracted from 100%, thus resulting in the proportion of the Raman non-active (noble gas) component(s) within the gas mixture. In case that there is only one Raman-active component, the proportion of the individual gas component is subtracted from 100% resulting in the proportion of the Raman non-active noble gas within the gas mixture. The assignment of the peak(s) in the measured spectrum to the individual gas component(s) can be done as known in the art, e.g. by comparing the wavelength(s) of the peak(s) with the wavelength(s) of the reference spectrum/spectra of the individual gas component(s).

The comparison of the measured Raman spectra with the reference Raman spectra is preferably accomplished by determining the ratio of the amplitudes (intensities) for each wavelength channel of the spectrograph. However, other comparison methods e.g. by means of the peak area or the like can be applied accordingly.

In case that a certain individual gas component reveals more than one Raman line, all lines are attenuated substantially evenly, so that, for the purpose of the invention, it is normally sufficient to evaluate only one Raman line for each gas component for determining the proportion of the individual gas component in the gas mixture.

The reference spectra comprising the wavelength positions and intensities are preferably determined by previous measurements and can be stored e.g. in a calibration matrix.

In case that the actual measuring conditions deviate from the measuring conditions of the reference spectra, the measured spectra have to be corrected, e.g. for the effects of pressure, temperature, and light intensity changes, using well-known algorithms.

The intensity of the gas-specific Raman signals also provides a direct measure for the partial pressure of each gas constituent and can consequently be applied for determining the partial pressure of each Raman-active gas component The gas mixture can be interpreted e.g. by means of the known multi-component analysis (which will be explained later) of the spectral information. According to Dalton's law of partial pressures, the sum of the partial pressures results in 100% of the total gas pressure in the system. The total gas pressure is also measured independently e.g. by a barometer. Thus, if the sum of the partial pressures of the Raman-active gas components of the gas mixture being analyzed adds up to less than the total gas pressure, the difference can be attributed to the partial pressure of the (Raman non-active) noble gas constituent.

The multi-component analysis method allows determining the concentrations of a number of known components in an arbitrary mixture of those components. Mathematically, this is accomplished by the following procedure, which is also called Singular Value Decomposition (SVD):

The reference spectrum of each pure component is determined and a limited number of spectral information pieces (e.g. intensities in certain wavelength channels) is stored as a column of a calibration matrix. If the system is calibrated e.g. for 10 different species, and the number of wavelength channels is 50, then the calibration matrix would be a 10×50 matrix.

The spectrum of the gas mixture to be measured is determined, and the spectral information is brought into the form of a vector (e.g. of 50 elements according to the above example). This vector is then multiplied with the pseudo-inverse of the calibration matrix This procedure delivers the concentrations of all components of the mixture.

The amount of the noble gas can thus be calculated with a high accuracy by quantitatively measuring all Raman active compounds of the gas mixture and by determining the difference to the ambient pressure.

In a respiratory system, the main components (or constituents) of the respiratory gas ($O_2$, $CO_2$, $N_2$, $N_2O$, and/or anesthetics) are generally all Raman-active, except of noble gas components such as xenon. In case of a xenon anesthesia, a mixture of air/Xe or $O_2$/Xe is supplied to the patient and an air/Xe/$CO_2$ mixture is exhaled. The amount of the noble gas can be calculated as shown above.

Figure 2:
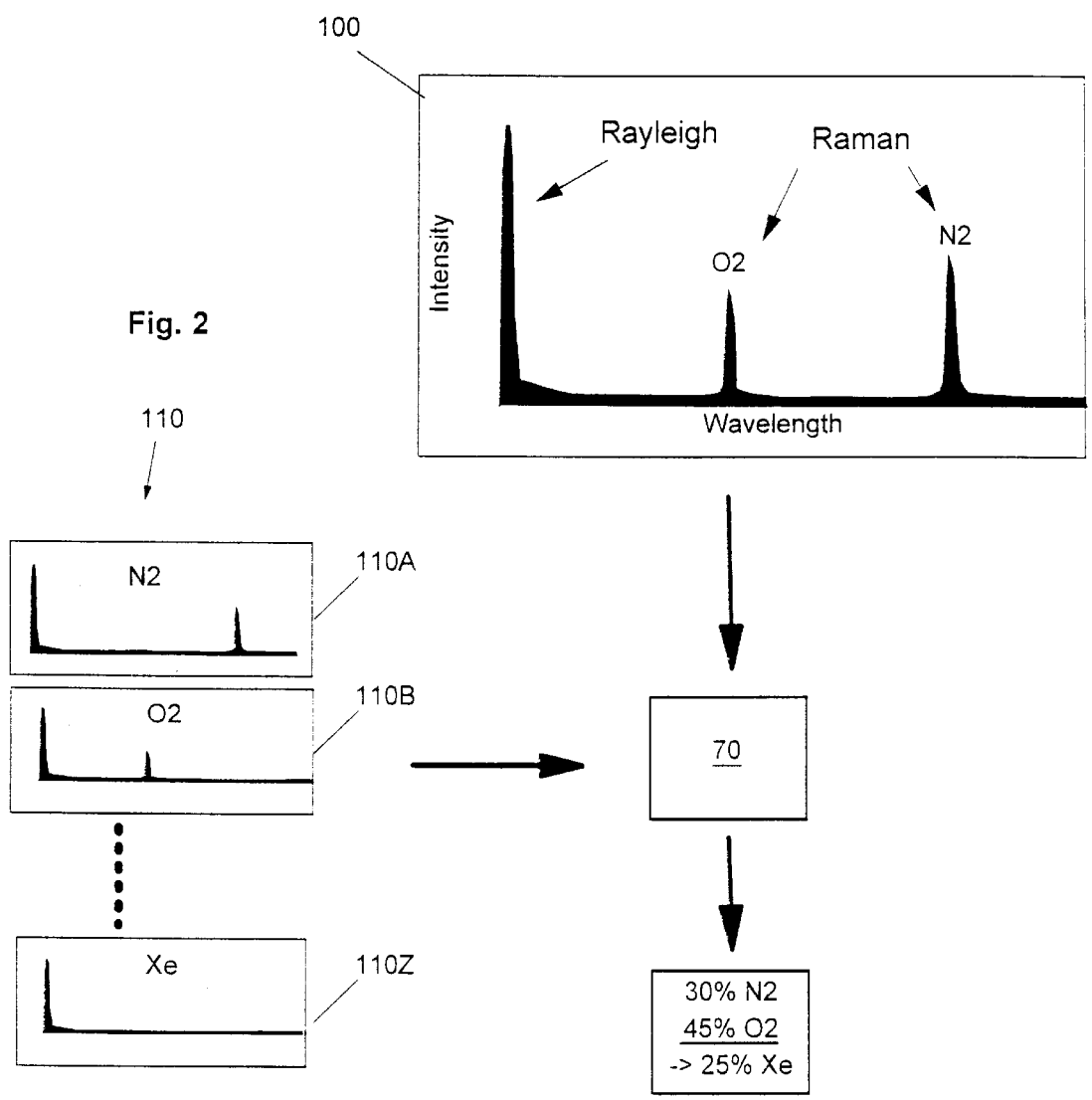
FIG. 2 shows an example of a measurement of a composition of a gas mixture comprising an unknown amount of xenon and an unknown amount of $N_2$ and $O_2$.

FIG. 2 shows an example of a measurement of a composition of a gas mixture comprising an unknown amount of xenon and an unknown amount of a number of other gas constituents, in this example $N_2$ and $O_2$. The spectrograph 60 measures the spectrum 100 of the gas mixture. The wavelength position and intensities of a plurality of Raman lines are stored in a calibration matrix 110 with a plurality of individual reference spectra 110A . . . 110Z for several gas constituents. As explained above, the (reference) spectrum 110Z for xenon does not show a Raman line.

The measured spectrum 100 of the gas mixture is compared with the respective reference spectra 110A, 110B of the calibration matrix 110. The proportions of the peak levels from the reference spectra 110A, 110B, and 110Z to the measured spectrum 100 provides a direct measure for the proportions of the individual components $N_2$ and $O_2$ in the gas mixture. In the example of FIG. 2, the wavelength and characteristics of the measured peaks refer to $N_2$ and $O_2$. The peak $N_2$ represents 30% of the reference peak for $N_2$ in the reference spectrum 110A, and the peak $O_2$ represents 45% of the reference peak for $O_2$ in the reference spectrum 110B. The sum of the $N_2$ and the $O_2$ ratio is 75%, so that the gas mixture comprises 25% Xe (as the difference to 100%).

Accordingly, the determined partial pressures in the example of FIG. 2 would be 300 mbar for $N_2$ and 450 mbar for $O_2$. The sum of the partial pressures of $N_2$ and $O_2$ ratio is 750 mbar, whereas the total gas pressure in the sample cell 30 shall be 1 bar, so that the gas mixture comprises a partial pressure of 250 mbar Xe (as the difference to the total gas pressure).

According to the second aspect of the invention, the composition of the gas mixture can also be determined by analyzing the Raman scattering in combination with the Rayleigh scattering. Although noble gases are Raman non-active, they contribute, as any gas, to the Rayleigh scattering (as the light scattering at the wavelength of the incident light). Each one of the reference spectra 110 in FIG. 2 shows at the left side the intensity of the Rayleigh line for the pure component Based on the measured Raman spectrum, the expected intensities of the Rayleigh lines of the Raman-active gases in the gas mixture are determined. The amount of the noble gas in the gas mixture is represented by the difference of the summed up Rayleigh lines of the Raman-active gases to the Rayleigh line in the measured spectrum.

Each peak in the measured Raman spectrum is analyzed and assigned to an individual gas component of the gas mixture. Since the peaks of each component are attenuated equally, it is sufficient to further analyze one representative peak for each determined gas component. The proportion of each representative peak in the measured spectrum to the corresponding peak in the respective reference spectrum is determined. For each gas component, the determined proportion is applied to the Rayleigh line in the respective reference spectrum thus yielding the expected intensity of the Rayleigh line for this component. The expected intensities of the Rayleigh lines are summed up and the sum is subtracted from the measured Rayleigh line of the gas mixture yielding an intensity difference resulting from the noble gas in the gas mixture. The proportion of the thus determined intensity difference to the intensity of the Rayleigh line in the reference spectrum of the respective noble gas represents the proportion of the noble gas in the gas mixture.

According to the third aspect, the result of the determining according to the first aspect is checked using the Rayleigh lines of the measured spectrum and the reference spectrum. For each identified component of the gas mixture, the intensity of the Rayleigh line corresponding to the (determined) proportion of the component in the gas mixture is determined and summed up. In case that the intensity of the summed up individual Rayleigh lines equals the intensity of the measured Rayleigh line, the composition of a gas mixture has been determined correctly.

In the embodiment as described above, the calibration vector of pure noble gas consists of only one Rayleigh line and no Raman line in the reference spectrum (cf. 110Z for xenon). A multi-component analysis of the Raman spectrum including the Rayleigh line thus provides the concentration of the noble gas as well as the concentrations of the other Raman-active gases.

It is to be understood that the Rayleigh line is normally blinded out for the Raman spectroscopy. However, for the purpose of the invention, the Raman spectrometer in the spectrograph 60 is preferably modified in a way that at least a small off-shot of the Rayleigh line can be measured (concurrently) with the Raman lines.

A possibility for measuring the Rayleigh intensity consists of employing a modified optical filter instead of the usual Rayleigh-blocking filter. The transmission characteristic of this filter is designed such that suitable amount of Rayleigh light is transmitted to the detector. An easy way of adjusting the amount of transmitted Rayleigh light is by tilting the filter.

Another possibility is to employ a conventional Rayleigh-blocking filter and to measure the Rayleigh light by a separate additional photodetector, which is placed at a suitable location. Such locations are for instance positions close to the laser beam. Alternatively, the light that is reflected off the Rayleigh filter, which consists only of Rayleigh light, can be directed to the additional photodetector.

It is clear that in case that the gas mixture comprises more than one Raman non-active component, the invention can be employed accordingly to determine the sum of the Raman non-active components. A detailed distinction of the Raman non-active components, if required, can be executed as known in the art, e.g. described in the introductionary part of the description.

Further more, the aspects of the invention can be applied as well in case of a stationary gas mixture as in case of a (continuous) gas flow. In the latter case, in particular the spectrograph 60 and the processing unit 70 should be adapted to the speed of the gas flow.

We claim:

1. A system for determining a composition of a gas mixture comprising an amount of one or more noble gases, the system comprising:

means for measuring a Raman spectrum of the gas mixture, and a processing unit for quantitatively determining, based on the contribution of one or more Raman-active gas(es) to the measured Raman spectrum, with respect to reference spectra of the Raman-active gas(es), the amount(s) of the Raman-active gas(es) in the gas mixture and for determining therefrom the amount of the one or more noble gases in the gas mixture.

2. The system of claim 1, further comprising reference means for comparing the measured Raman spectrum with one or more reference spectra, whereby the proportion of the measured spectrum to the reference spectrum or to each one of the reference spectra provides a measure for the proportion of the gas component represented by the respective reference spectrum in the gas mixture.

3. The system of claim 2, wherein the reference means comprises means for comparing one or more peaks of the measured Raman spectrum with one or more peaks in the one or more reference spectra, preferably by comparing the amplitudes and/or intensities of the peaks.

4. The system according to claim 1, wherein the processing unit comprises:

means for summing up the amounts of the Raman-active gases in the gas mixture, and means for subtracting the summed up amounts from the total amount of the gas mixture, whereby the subtracted amount represents the amount of the one or more noble gases.

5. The system according to claim 1, further comprising:

means for determining a partial pressure of the Raman-active gases in the gas mixture, means for summing up the determined partial pressures of the Raman-active gases in the gas mixture, and means for subtracting the summed up partial pressures from the total pressure of the gas mixture, whereby the subtracted pressure represents the partial pressure of the one or more noble gases.

6. The system according to claim 1, wherein the reference spectrum or each one of the reference spectra represents the Raman spectrum for a pure gas component or a defined gas mixture preferably determined under known conditions.

7. The system according to claim 1, further comprising:

a sample cell including the gas mixture, and means for emitting a light beam into the sample cell, whereby the processing unit is preferably coupled thereto for receiving information therefrom.

8. The system of claim 7, wherein the sample cell comprises pressure determining means and/or temperature determining means, whereby the processing unit is preferably coupled thereto for receiving information therefrom.

9. The system according to claim 1, further comprising:

means for measuring a Rayleigh spectrum of the gas mixture, and wherein the processing unit comprises analyzing means for quantitatively determining, based on the measured Raman spectrum, the expected intensity(s) of the Rayleigh line(s) of the Raman-active gas(es) in the gas mixture and for determining therefrom the amount of the one or more noble gases in the gas mixture.

10. The system according to claim 9, where in the analyzing means comprises:

means for determining an expected intensity of a Rayleigh line corresponding to the determined amount of each Raman-active gas, means for summing up the expected intensity(s) of the Rayleigh line(s), means for subtracting the summed up expected intensity (s) of the Rayleigh line(s) from the measured intensity of the Rayleigh line of the gas mixture, whereby the subtracted intensity represents the amount of the one or more noble gases.

11. A respiration gas monitor comprising a system according to claim 1 for monitoring a noble gas, preferably xenon.

12. A method for determining a composition of a gas mixture comprising an amount of one or more noble gases, the method comprising the steps of:

(a) measuring a Raman spectrum of the gas mixture, (b) quantitatively determining, based on the contribution of one or more Raman-active gas(es) to the measured Raman spectrum, with respect to reference spectra of the Raman-active gas(es), the amount(s) of the Raman-active gas(es) in the gas mixture, and (c) determining the amount of the one or more noble gases in the gas mixture based on the amount(s) of Raman-active gas(es) as determined in step (b).

13. The method of claim 12, wherein step (c) comprises a step of comparing the measured Raman spectrum with one or more reference spectra, whereby the proportion of the measured spectrum to the reference spectrum or to each one of the reference spectra provides a measure for the proportion of the gas component represented by the respective reference spectrum in the gas mixture.

14. The method of claim 12, wherein step (c) comprises the steps of summing up the amounts of the Raman-active gases in the gas mixture and subtracting the summed up amounts from the total amount of the gas mixture, whereby the subtracted amount represents the amount of the one or more noble gases.

15. The method according to claim 12, further comprising the steps of:

measuring a Rayleigh spectrum of the gas mixture, quantitatively determining, based on the measured Raman spectrum, the expected intensity(s) of the Rayleigh line(s) of the Raman-active gas(es) in the gas mixture, and determining from the expected intensity(s) the amount of the one or more noble gases in the gas mixture.

16. The method according to claim 15, comprising the steps of:

determining an expected intensity of a Rayleigh line corresponding to the determined amount of each Raman-active gas, summing up the expected intensity(s) of the Rayleigh line(s), subtracting the summed up expected intensity(s) of the Rayleigh line(s) from the measured intensity of the Rayleigh line of the gas mixture, whereby the subtracted intensity represents the amount of the one or more noble gases.

* * * * *